ns011124755B2

United States Patent
Ariga et al.

(10) Patent No.: US 11,124,755 B2
(45) Date of Patent: Sep. 21, 2021

(54) CELL CULTURE MONITORING SYSTEM

(71) Applicant: OLYMPUS CORPORATION, Hachioji (JP)

(72) Inventors: Naohiro Ariga, Tokyo (JP); Toshiyuki Hattori, Tokyo (JP); Mina Kobayashi, Tokyo (JP); Ayumu Sakurai, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 612 days.

(21) Appl. No.: 15/987,513

(22) Filed: May 23, 2018

(65) Prior Publication Data
US 2018/0346869 A1 Dec. 6, 2018

(30) Foreign Application Priority Data
Jun. 1, 2017 (JP) .............................. JP2017-108900

(51) Int. Cl.
*C12M 1/34* (2006.01)
*C12M 1/00* (2006.01)
*C12M 1/36* (2006.01)

(52) U.S. Cl.
CPC ............ *C12M 41/46* (2013.01); *C12M 41/14* (2013.01); *C12M 41/36* (2013.01); *C12M 41/48* (2013.01)

(58) Field of Classification Search
None
See application file for complete search history.

(56) References Cited

U.S. PATENT DOCUMENTS

2002/0055166 A1* 5/2002 Cannon .................. C12M 23/48
435/286.5
2005/0051723 A1 3/2005 Neagle et al.
(Continued)

FOREIGN PATENT DOCUMENTS

EP 2484750 A1 8/2012
JP 2009533053 A 9/2009
(Continued)

OTHER PUBLICATIONS

Extended European Search Report (EESR) dated Oct. 12, 2018 issued in counterpart European Application No. 18174255.2.

*Primary Examiner* — William H. Beisner
(74) *Attorney, Agent, or Firm* — Holtz, Holtz & Volek PC

(57) ABSTRACT

A cell culture monitoring system includes measuring units housed in an incubator and each equipped with an indicator, the measuring units each measuring a state of cells in a culture container mounted therein; and an administration unit. The administration unit includes a receiver that receives, from each of the measuring units, a state of the cells measured, the state being associated with identification information of the measuring unit; an analyzer that analyzes the state of the cells and computes information indicating a culture state; a storage that stores, in association with each other, the information indicating the culture state and the identification information; a display that displays, in association with each other, the information indicating the culture state and an identification based on the identification information; and a controller that controls the indicators so that each of the indicators displays the identification corresponding to the identification displayed on the display.

9 Claims, 3 Drawing Sheets

(56) References Cited

U.S. PATENT DOCUMENTS

2008/0318307 A1 12/2008 Spittle et al.
2013/0316442 A1 11/2013 Meurville et al.

FOREIGN PATENT DOCUMENTS

| WO | 2005009126 A1 | 2/2005 |
| WO | 2007120619 A2 | 10/2007 |
| WO | 2017079682 A1 | 5/2017 |

* cited by examiner

FIG. 4

| ID INFORMATION | ID INDICATOR INFORMATION | CULTURE STATE INFORMATION |
|---|---|---|
| 3A | 1 | S1 |
| 3B | 2 | S2 |
| 3C | 3 | S3 |
| 3D | 4 | S4 |

CELL CULTURE MONITORING SYSTEM

CROSS-REFERENCE TO RELATED APPLICATIONS

This application is based on Japanese Patent Application No. 2017-108900, the content of which is incorporated herein by reference.

TECHNICAL FIELD

The present invention relates to a cell culture monitoring system.

BACKGROUND ART

There is a known culture state monitoring apparatus in which multiple culture dishes are housed inside an incubator, and the measurement results from pH sensors and temperature sensors installed on the culture dishes are wirelessly transmitted to a data recording device outside the incubator and displayed on a computer coupled to the data recording device (for example, see PTL 1).

CITATION LIST

Patent Literature

{PTL 1} Japanese Translation of PCT International Application, Publication No. 2009-533053

SUMMARY OF INVENTION

An aspect of the present invention provides a cell culture monitoring system that includes a plurality of measuring units housed in an incubator and each equipped with an identification indicator unit, each of the measuring units measuring a state of cells contained in a culture container mounted thereon; and an administration unit disposed outside the incubator, the administration unit communicating with the plurality of measuring units. The administration unit includes a receiver unit that receives, from each of the measuring units, information indicating a state of the cells measured, the information being associated with identification information of the corresponding measuring unit; an analyzing unit that analyzes the information indicating the state of the cells received by the receiver unit to compute information indicating a culture state; a storage unit that stores, in association with each other, the information indicating the culture state, which has been computed by the analyzing unit, and the identification information, which has been transmitted from the measuring units; a display unit that displays, in association with each other, the information indicating the culture state, which is stored in the storage unit, and an identification, which is based on the identification information; and a control unit that controls the identification indicator units of the measuring units so that each of the identification indicator units displays the identification corresponding to the identification displayed on the display unit.

BRIEF DESCRIPTION OF DRAWINGS

FIG. 4 is a table indicating measuring unit ID information, ID indicator information, and culture state information associated with one another and stored in the storage unit of the cell culture monitoring system illustrated in FIG. 1.

DESCRIPTION OF EMBODIMENTS

A cell culture monitoring system 1 according to one embodiment of the present invention will now be described with reference to the drawings.

Figure 1:
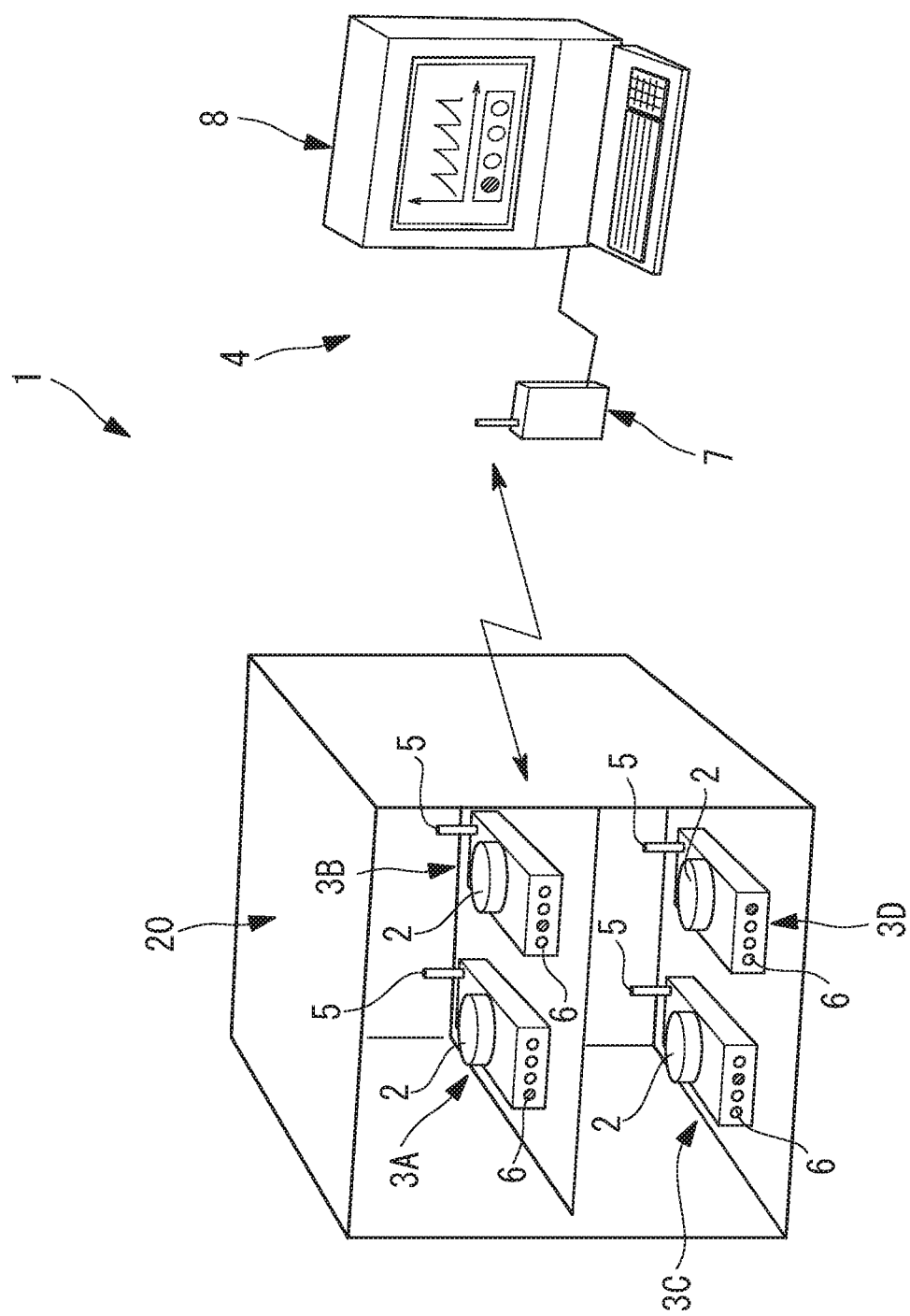
FIG. 1 is an overall view of a cell culture monitoring system according to one embodiment of the present invention.

As illustrated in FIG. 1, the cell culture monitoring system 1 according to this embodiment includes measuring units 3A, 3B, 3C, and 3D placed in an incubator 20 maintained at a particular temperature and a particular humidity, and an administration unit 4 disposed outside the incubator 20. A culture container 2 containing cells and a medium is mounted on each of the measuring units 3A, 3B, 3C, and 3D.

The measuring units 3A, 3B, 3C, and 3D are each equipped with a box-shaped casing that houses the culture container 2 that contains cells and a medium, and are each configured to acquire, over time, the information (cell state information, for example, an image of the cells) that indicates the state of growing cells attached to the bottom surface of the culture container 2. The measuring units 3A, 3B, 3C, and 3D respectively include storage units (not illustrated) that store the identification (ID) information of the measuring units 3A, 3B, 3C, and 3D and the acquired cell state information, and transmitter-receiver units 5 that associate the ID information with the cell state information stored in the storage unit, transmit the ID information and the associated cell state information to the exterior, and receive signals from the exterior.

In this embodiment, the incubator 20 can accommodate four measuring units 3A, 3B, 3C, and 3D simultaneously. Each of the measuring units 3A, 3B, 3C, and 3D is equipped with multiple (for example, four in this embodiment) light-emitting diodes (LEDs, ID indicator unit) 6 arranged in a row at a position easily recognizable (for example, at the front surface or the top) when the measuring units 3A, 3B, 3C, and 3D are placed inside the incubator 20. In each of the measuring units 3A, 3B, 3C, and 3D, one of the LEDs 6 is lighted, and since the position of the lighted LED 6 differs among the measuring units 3A, 3B, 3C, and 3D, the LEDs 6 function as the ID indicator unique to each measuring unit. In the drawing, the lighted LEDs 6 are shaded.

The administration unit 4 is equipped with a transmitter-receiver device (receiver unit) 7 that transmits and receives information to and from the exterior, and an information processing device (for example, a personal computer (PC) system) 8 that generates the information to be sent from the transmitter-receiver device 7 and processes the information received.

Figure 2:
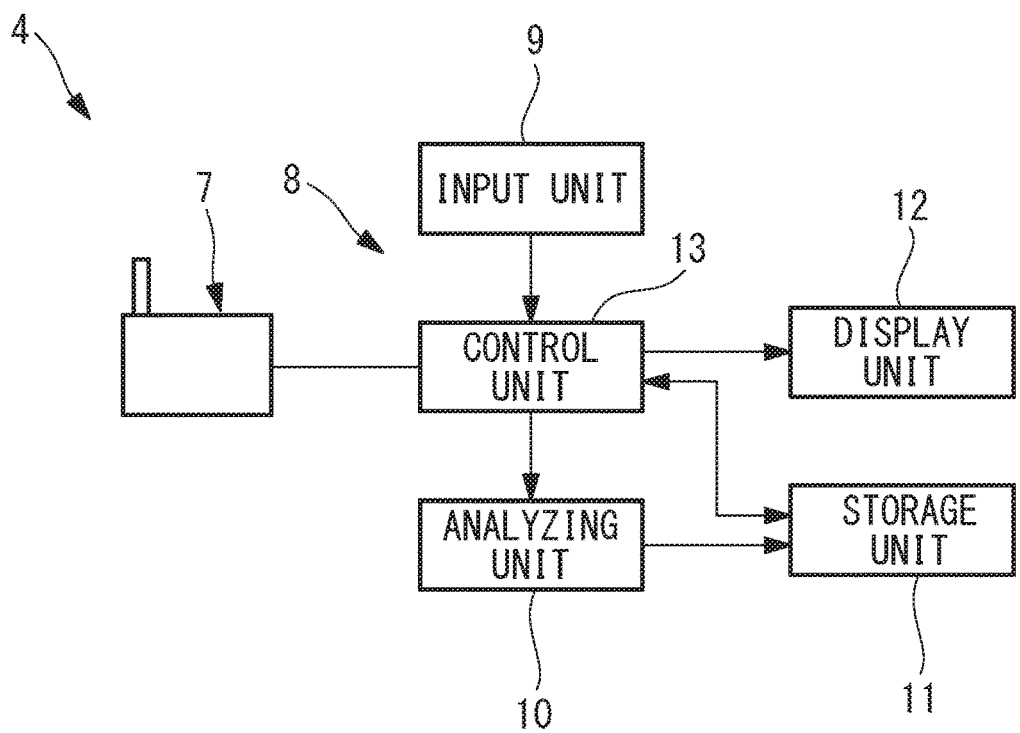
FIG. 2 is a block diagram illustrating an administration unit of the cell culture monitoring system illustrated in FIG. 1.

As illustrated in FIG. 2, the information processing device 8 is equipped with an input unit (for example, a keyboard, a mouse, or a touch panel) 9 through which the user performs inputs; an analyzing unit (for example, a CPU and a analysis program) 10 that analyzes the cell state information transmitted from the measuring units 3A, 3B, 3C, and 3D and computes the information indicating the culture state (culture state information); a storage unit (for example, a hard disk or a memory of a PC or a storage on the network)

11 that stores the culture state information, which has been computed in the analyzing unit 10, in association with the ID information received by the transmitter-receiver device 7; a display unit (for example, an LCD monitor or a touch panel) 12 that displays the culture state information computed in the analyzing unit 10 and other information; and a control unit (for example, a CPU and a control program) 13 that outputs signals for controlling the measuring units 3A, 3B, 3C, and 3D.

The input unit 9 is an input device, such as a keyboard or a mouse, and is used to select which analysis result for which of the measuring units 3A, 3B, 3C, and 3D is to be displayed.

The analyzing unit 10 analyzes the cell state information received by the transmitter-receiver device 7 for the measuring unit 3A, 3B, 3C, or 3D selected through the input unit 9, and computes the culture state information, such as the number of cells, the cell density, etc. In the example illustrated in FIG. 3, changes over time in the number of cells or the cell density for each culture period separated by subculture are output.

The storage unit 11 stores, as mentioned above, the culture state information and the associated ID information of the measuring units 3A, 3B, 3C, and 3D. Furthermore, as illustrated in FIG. 4, the storage unit 11 also stores the information (ID indicator information) corresponding to an ID indicator unique to the ID information. The ID indicator information is allocated by the control unit 13. The unique ID indicator information is, for example, the number that indicates the position of the lighted LED out of the four LEDs 6, counted from the left.

Figure 3:
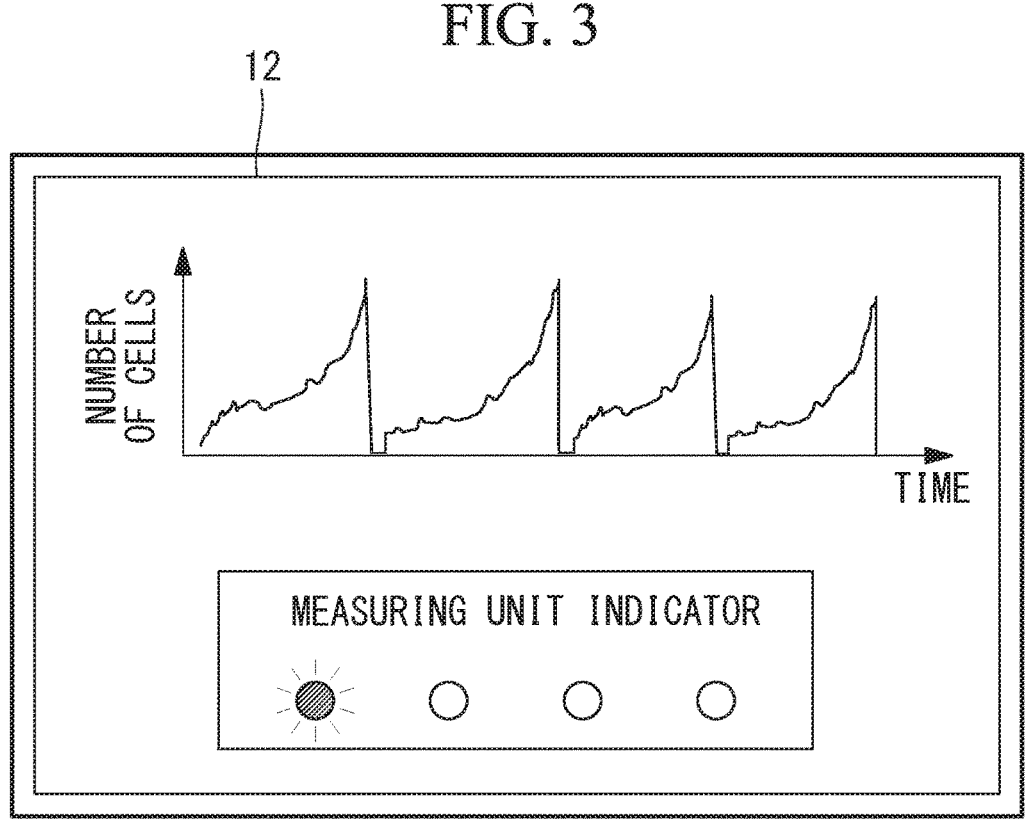
FIG. 3 is a diagram illustrating an example of a display on a display unit of the cell culture monitoring system illustrated in FIG. 1.

The display unit 12 displays the culture state information computed in the analyzing unit 10. The display unit 12 also directly displays the ID indicator information associated with the ID information of the measuring unit 3A, 3B, 3C, or 3D stored in the storage unit 11, or displays information generated on the basis of the ID indicator information. For example, in this embodiment, the number corresponding to the ID indicator may be directly displayed; alternatively, as illustrated in FIG. 3, an image that simulates the row of the LEDs 6 in the measuring unit 3A, 3B, 3C, or 3D and shows the lighted LED 6 at the position corresponding to that number may be displayed on the basis of the number.

The control unit 13 distinguishes the measuring units 3A, 3B, 3C, and 3D connected thereto on the basis of the ID information sent from each of the measuring units 3A, 3B, 3C, and 3D, and allocates ID indicator information unique to the corresponding ID information. Allocation of the ID indicator information by the control unit 13 may be done in the order in which the ID information has been transmitted. Alternatively, the control unit 13 may request transmission of the ID information to the measuring units 3A, 3B, 3C, and 3D, and after identifying all of the measuring units 3A, 3B, 3C, and 3D connected thereto, allocation may be performed according to a desired rule, such as the ascending order of the ID information.

When the cell state information is transmitted from the measuring units 3A, 3B, 3C, and 3D, the control unit 13 commands the analyzing unit 10 to analyze the cell state information.

When information regarding the measuring unit 3A, 3B, 3C, or 3D for which the user wants to monitor is input through the input unit 9, the control unit 13 reads out the culture state information, which is stored in the storage unit 11, associated with the ID information of that measuring unit 3A, 3B, 3C, or 3D, and commands the display unit 12 to display that information.

The control unit 13 also transmits the ID information and the ID indicator information of the measuring units 3A, 3B, 3C, and 3D via the transmitter-receiver device 7.

In each of the measuring units 3A, 3B, 3C, and 3D, when the information containing the ID information of its own is transmitted, the measuring unit lights the LED 6 indicated by the ID indicator information among the LEDs 6 of its own on the basis of the ID indicator information transmitted together with the ID information.

The effects of the cell culture monitoring system 1 according to this embodiment, configured as described above, will now be described.

In order to monitor the culture state of the cells by using the cell culture monitoring system 1 of this embodiment, the culture containers 2 each containing cells and a medium and respectively being mounted on the measuring units 3A, 3B, 3C, and 3D are put inside the incubator 20, and then observation is started.

Once observation is started, images of cells, which constitute cell state information, are acquired on a regular basis, and the acquired image information is sequentially stored in the storage unit. The image information in chronological order stored in the storage unit is associated with the ID information of the measuring units 3A, 3B, 3C, and 3D and transmitted, on a regular basis or as needed, to the administration unit 4 via the transmitter-receiver units 5.

When the administration unit 4 receives the ID information and the cell images sent from the measuring units 3A, 3B, 3C, and 3D, the control unit 13 allocates unique ID indicator information to the ID information of the measuring units 3A, 3B, 3C, and 3D connected thereto and commands the storage unit 11 to store the ID indicator information.

When the ID indicator information is allocated, the control unit 13 sends the ID indicator information along with the ID information and thereby controls the measuring units 3A, 3B, 3C, and 3D so that the LEDs 6 that are indicated in the ID indicator information are lighted in the measuring units 3A, 3B, 3C, and 3D having the corresponding ID information.

When an image of cells is transmitted from one of the measuring units 3A, 3B, 3C, and 3D, the control unit 13 transmits the transmitted image of the cells to the analyzing unit 10, and commands the analyzing unit 10 to compute the culture state information S1, S2, S3, or S4. As illustrated in FIG. 4, the computed culture state information is associated with the ID information of the measuring unit 3A, 3B, 3C, or 3D and stored in the storage unit 11.

When the user has input, through the input unit 9, the ID information of the measuring unit 3A, 3B, 3C, or 3D whose culture state of the cells the user wishes to confirm, the control unit 13 reads out the culture state information along with the ID indicator information associated with the input ID information and stored in the storage unit 11, and displays that information on the display unit 12, as illustrated in FIG. 3.

According to the cell culture monitoring system 1 of this embodiment, on the basis of the ID indicator information allocated by the control unit, the positions of the lighted LEDs 6 of the measuring units 3A, 3B, 3C, and 3D are determined, and an image in which the LED 6 at the position indicated by the ID indicator information is lighted is displayed on the display unit 12. Thus, the culture state information displayed on the display unit 12 can be unfailingly identified as being measured by one of the measuring units 3A, 3B, 3C, and 3D which has the lighted LED 6 at the same position as that in the image displayed on the display unit 12.

In other words, even when multiple measuring units 3A, 3B, 3C, and 3D having appearances that are not distinguishable from one another are housed in the same incubator 20, the LEDs 6 of the measuring units 3A, 3B, 3C, and 3D are controlled according to the ID information and the ID indicator information administered by the administration unit 4, and, thus, the user is prevented from misidentifying the culture containers 2.

In this embodiment, each of the measuring units 3A, 3B, 3C, and 3D is equipped with multiple LEDs 6 that are arranged in a row, and the ID is displayed through the position of the lighted LED 6. In this embodiment, one of the four LEDs 6 arranged in a row is lighted and used as the ID indicator for distinguishing the four measuring units 3A, 3B, 3C, and 3D from one another; however, for example, two or more LEDs 6 may be lighted simultaneously so that, even when there are more measuring units 3A, 3B, 3C, and 3D than there are LEDs 6, the measuring units 3A, 3B, 3C, and 3D can be distinguished from one another by the combination of the lighted LEDs 6.

Instead of using the position of the lighted LED 6 to display the ID, LEDs 6 that can change the color of the light emitted may be used so that the color of light emitted from the LEDs 6 differs for each of the measuring units 3A, 3B, 3C, and 3D and can be used as the ID indicator.

Although the LEDs 6 are used to display the ID, the measuring units 3A, 3B, 3C, and 3D may instead each be equipped with a sound source, and the measuring units 3A, 3B, 3C, and 3D may be configured to output sound pitches or melodies that are different from one another to indicate the ID.

Alternatively, a device, such as electronic paper or a liquid crystal display, that can display characters or signs may be employed as the ID indicator units of the measuring units 3A, 3B, 3C, and 3D, and a character or sign set to correspond to the ID information of each of the measuring units 3A, 3B, 3C, and 3D may be used to display the ID. For example, when the measuring units 3A, 3B, 3C, and 3D are used by different users, the names of the users may be displayed.

In this embodiment, the cell culture monitoring system 1 is equipped with four measuring units 3A, 3B, 3C, and 3D; alternatively, the cell culture monitoring system 1 may be equipped with two, three, or five or more measuring units.

Moreover, in this embodiment, an example in which the acquired cell state information is temporarily stored in the storage units of the measuring units 3A, 3B, 3C, and 3D is described. Alternatively, the acquired cell state information may be transmitted to the administration unit 4 without storing the information.

As a result, the above-described embodiment leads to the following aspect.

An aspect of the present invention provides a cell culture monitoring system that includes a plurality of measuring units housed in an incubator and each equipped with an identification indicator unit, each of the measuring units measuring a state of cells contained in a culture container mounted thereon; and an administration unit disposed outside the incubator, the administration unit communicating with the plurality of measuring units. The administration unit includes a receiver unit that receives, from each of the measuring units, information indicating a state of the cells measured, the information being associated with identification information of the corresponding measuring unit; an analyzing unit that analyzes the information indicating the state of the cells received by the receiver unit to compute information indicating a culture state; a storage unit that stores, in association with each other, the information indicating the culture state, which has been computed by the analyzing unit, and the identification information, which has been transmitted from the measuring units; a display unit that displays, in association with each other, the information indicating the culture state, which is stored in the storage unit, and an identification, which is based on the identification information; and a control unit that controls the identification indicator units of the measuring units so that each of the identification indicator units displays the identification corresponding to the identification displayed on the display unit.

According to this embodiment, the measuring units, each having a cell-containing culture container mounted therein, are housed in the incubator, and when the state of the cells in the culture container is measured by operating each measuring unit, the state of the cells measured and the identification information of the measuring unit are transmitted to the exterior of the incubator and received by the receiver unit of the administration unit.

In the administration unit, the state of the cells received is analyzed by the analyzing unit, which computes the culture state, and the culture state is associated with the identification information received and is stored in the storing unit. Moreover, the stored information indicating the culture state and the identification based on the identification information are associated with each other and displayed on the display unit.

At the same time, the control unit of the administration unit controls the identification indicator units of the measuring units, so that the identification corresponding to the identification displayed on the display unit is displayed in each identification indicator unit.

The user can check the identification displayed on the display unit and the identification in the identification indicator unit of each measuring unit in the incubator; thus, the user can unfailingly identify the measuring unit on which the culture container corresponding to the culture state displayed on the display unit is mounted.

In the aspect described above, the identification indicator unit may include a plurality of light-emitting diodes (LEDs) arranged in a row, and the identification may be a position of a lighted light-emitting diode of the light-emitting diodes arranged in a row.

In this manner, in the identification indicator unit, one of the LEDs is lighted, and the display unit displays the information regarding the position of the lighted LED. Thus, the user can easily identify the measuring unit on which the culture container corresponding to the culture state displayed on the display unit is mounted.

In the aspect described above, the identification indicator unit may include a light-emitting diode, emitted light from which can be changed in color, and the identification may be the color of the light emitted from the light-emitting diode.

In this manner, in the identification indicator unit, the light-emitting diode is lighted to emit light of a particular color, and the information regarding the color of the lighted LED is displayed on the display unit. Thus, the user can easily identify the measuring unit on which the culture container corresponding to the culture state displayed on the display unit is mounted.

In the aspect described above, the identification indicator unit may include a sound source, from which generated sound can be changed, and, the identification may be a sound pitch or melody generated from the sound source.

In this manner, in the identification indicator unit, sound of a particular pitch or a melody is output from the sound source, and, on the display unit, the information regarding the sound output is displayed. Thus, the user can easily identify the measuring unit on which the culture container corresponding to the culture state displayed on the display unit is mounted.

In the aspect described above, the identification indicator unit may include a display that can display characters or signs, and the identification may be a character or sign set to correspond to the identification information of the measuring unit.

In this manner, in the identification indicator unit, the character or sign corresponding to the identification information is displayed on the display, and, on the display unit, the information of the displayed character or sign is displayed. Thus, the user can easily identify the measuring unit on which the culture container corresponding to the culture state displayed on the display unit is mounted.

The present invention offers an advantageous effect in that an erroneous operation by the user can be prevented with more certainty.

REFERENCE SIGNS LIST 1 cell culture monitoring system
2 culture container
3A, 3B, 3C, 3D measuring unit
4 administration unit
6 LED (ID indicator unit)
7 transmitter-receiver device (receiver unit)
10 analyzing unit
11 storage unit
12 display unit
13 control unit
20 incubator

The invention claimed is:

1. A cell culture monitoring system comprising:
a plurality of measuring units housed in an incubator and each equipped with an identification indicator, each of the plurality of measuring units being configured to measure a state of cells contained in a culture container mounted thereon; and
an administration unit disposed outside the incubator, the administration unit being configured to communicate with the plurality of measuring units, the administration unit comprising a display and at least one hardware processor,
wherein the at least one hardware processor is configured to:
receive, from each of the measuring units, information indicating a state of the cells measured, the information being associated with identification information of the corresponding measuring unit;
analyze the received information indicating the state of the cells to compute information indicating a culture state;
store, in association with each other, for each measuring unit, the computed information indicating the culture state of the measuring unit, the identification information transmitted from the measuring unit, and identification indicator information corresponding to the identification information of the measuring unit;
display, on the display, in association with each other, the stored information indicating the culture state, and an image indicating an identification which is based on the identification indicator information corresponding to the identification information, for each respective measuring unit; and
control the identification indicators of the measuring units so that each of the identification indicators displays the identification corresponding to the identification indicated in the image displayed on the display for that measuring unit,
wherein, in controlling the identification indicators, the at least one hardware processor is configured to:
receive an identification information input by a user corresponding to the identification information of one of the plurality of measuring units;
transmit, to the measuring unit corresponding to the received identification information, the received identification information and the corresponding identification indicator information to control the identification indicator of the corresponding measuring unit to display the corresponding identification based on the corresponding identification indicator information, and
transmit, to the display, the stored information indicating the culture state corresponding to the identification indicator information and the received identification information to control the display to display the stored information indicating the culture state and the image indicating the identification based on the identification indicator information corresponding to the received identification information.

2. The cell culture monitoring system according to claim 1, wherein each identification indicator comprises a plurality of light-emitting diodes arranged in a row, and
the identification is a position of a lighted light-emitting diode of the light-emitting diodes arranged in a row.

3. The cell culture monitoring system according to claim 1, wherein each identification indicator comprises a light-emitting diode, emitted light from which can be changed in color, and
the identification is the color of the light emitted from the light-emitting diode.

4. The cell culture monitoring system according to claim 1, wherein each identification indicator comprises a sound source, from which generated sound can be changed, and
the identification is a sound pitch or melody generated from the sound source.

5. The cell culture monitoring system according to claim 1, wherein each identification indicator comprises a display that can display characters or signs, and
the identification is a character or sign set to correspond to the identification information of the measuring unit.

6. The cell culture monitoring system according to claim 1, wherein the information indicating the state of the cells comprises an image of the cells.

7. A non-transitory computer-readable storage medium having stored thereon a program that is executable by a computer that is configured to communicate with a plurality of measuring units each comprising an identification indicator, each measuring unit being configured to measure a state of cells contained in a culture container mounted thereon, the program being executable by the computer to control the computer to perform functions comprising:
receiving, from each of the measuring units, information indicating a state of the cells measured, the information being associated with identification information of the corresponding measuring unit;
analyzing the received information indicating the state of the cells to compute information indicating a culture state;
storing, in association with each other, for each measuring unit, the computed information indicating the culture state of the measuring unit, the identification information transmitted from the measuring unit, and identification indicator information corresponding to the identification information of the measuring unit;

displaying, on a display of the computer, in association with each other, the stored information indicating the culture state, and an image indicating an identification which is based on the identification indicator information corresponding to the identification information, for each respective measuring unit; and controlling the identification indicators of the measuring units so that each of the identification indicators displays the identification corresponding to the identification indicated in the image displayed on the display for that measuring unit, wherein the controlling of the identification indicators comprises:

receiving an identification information input by a user corresponding to the identification information of one of the plurality of measuring units;

transmitting, to the measuring unit corresponding to the received identification information, the received identification information and the corresponding identification indicator information to control the identification indicator of the corresponding measuring unit to display the corresponding identification based on the corresponding identification indicator information, and transmitting, to the display, the stored information indicating the culture state corresponding to the identification indicator information and the received identification information to control the display to display the stored information indicating the culture state and the image indicating the identification based on the identification indicator information corresponding to the received identification information.

8. A measuring unit housed in an incubator, the measuring unit being configured to measure a state of cells contained in a culture container mounted thereon, comprising:

an identification indicator; and a transmitter-receiver configured to communicate with an administration unit disposed outside the incubator, the administration unit comprises a display and at least one hardware processor, wherein the transmitter-receiver is configured to transmit, to the administration unit, information indicating a state of the cells measured, the information being associated with identification information of the measuring unit;

wherein the at least one hardware processor is configured to analyze the information indicating the state of the cells received from the measuring unit to compute information indicating a culture state, (ii) store, in association with each other, the computed information indicating the culture state, the identification information transmitted from the measuring unit, and identification indicator information corresponding to the identification information, and (iii) display, on the display, in association with each other, the stored information indicating the culture state, and an image indicating an identification which is based on the identification indicator information corresponding to the identification information; and wherein the transmitter-receiver is configured to receive, from the administration unit, information for controlling the identification indicator so that the identification indicator displays the identification corresponding to the identification indicated in the image displayed on the display, and the measuring unit is configured to control the identification indicator to display the identification in accordance with the received information;

wherein, in controlling the identification indicator:

the at least one hardware processor of the administration unit is configured to (i) receive an identification information input by a user corresponding to the identification information of measuring unit, (ii) transmit, to the display, the stored information indicating the culture state corresponding to the received identification information and the corresponding identification indicator information to control the display to display the stored information indicating the culture state and the image indicating the identification based on the identification indicator information corresponding to the received identification information, and (iii) transmit, to the measuring unit, the received identification information and the corresponding identification indicator information; and the measuring unit is configured to receive, via, the transmitter-receiver, the identification information input by the user and the corresponding identification indicator information transmitted from the administration unit, as said information for controlling the identification indicator, and control the identification indicator to display the identification based on the received identification indicator information.

9. An administration unit disposed outside an incubator, the administration unit configured to communicate with a plurality of measuring units, the plurality of measuring units housed in the incubator, each of the plurality of measuring units comprising an identification indicator, each of the plurality of measuring units being configured to measure a state of cells contained in a culture container mounted thereon, the administration unit comprising:

a display; and at least one hardware processor configured to:

receive, from each of the measuring units, information indicating a state of the cells measured, the information being associated with identification information of the corresponding measuring unit;

analyze the received information indicating the state of the cells to compute information indicating a culture state;

store, in association with each other, for each measuring unit, the computed information indicating the culture state of the measuring unit, the identification information transmitted from the measuring unit, and identification indicator information corresponding to the identification information of the measuring unit;

display, on the display, in association with each other, the stored information indicating the culture state, and an image indicating an identification which is based on the identification indicator information corresponding to the identification information, for each respective measuring unit; and control the identification indicators of the measuring units so that each of the identification indicators displays the identification corresponding to the identification indicated in the image displayed on the display for that measuring unit, wherein, in controlling the identification indicators, the at least one hardware processor is configured to:

receive an identification information input by a user corresponding to the identification information of one of the plurality of measuring units;

transmit, to the measuring unit corresponding to the received identification information, the received identification information and the corresponding identification indicator information to control the identification indicator of the corresponding measuring unit to display the corresponding identification based on the corresponding identification indicator information, and transmit, to the display, the stored information indicating the culture state corresponding to the identification indicator information and the received identification information to control the display to display the stored information indicating the culture state and the image indicating the identification based on the identification indicator information corresponding to the received identification information.

\* \* \* \* \*